(12) United States Patent
Hinchet et al.

(10) Patent No.: US 11,385,719 B2
(45) Date of Patent: Jul. 12, 2022

(54) ELECTROSTATIC BRAKE-BASED HAPTIC DEVICE

(71) Applicant: ECOLE POLYTECHNIQUE FEDERALE DE LAUSANNE (EPFL), Lausanne (CH)

(72) Inventors: Ronan Hinchet, Pontarlier (FR); Herbert Shea, Cormondreche (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 17/258,511

(22) PCT Filed: Jul. 10, 2018

(86) PCT No.: PCT/IB2018/055075
§ 371 (c)(1),
(2) Date: Jan. 7, 2021

(87) PCT Pub. No.: WO2020/012219
PCT Pub. Date: Jan. 16, 2020

(65) Prior Publication Data
US 2021/0271326 A1 Sep. 2, 2021

(51) Int. Cl.
*G06F 3/01* (2006.01)
*B06B 1/02* (2006.01)

(52) U.S. Cl.
CPC ............ *G06F 3/016* (2013.01); *B06B 1/0292* (2013.01); *G06F 3/014* (2013.01)

(58) Field of Classification Search
None
See application file for complete search history.

(56) References Cited

U.S. PATENT DOCUMENTS

| | | | |
|---|---|---|---|
| 2004/0201443 A1* | 10/2004 | Kaneko | H02N 2/023 337/100 |
| 2010/0041521 A1 | 2/2010 | Ingvast et al. | |
| 2013/0072829 A1 | 3/2013 | Fausti et al. | |
| 2013/0219585 A1 | 8/2013 | Bergelin et al. | |
| 2015/0355710 A1* | 12/2015 | Modarres | G09G 5/003 345/173 |
| 2016/0015590 A1 | 1/2016 | Arata et al. | |
| 2016/0361179 A1 | 12/2016 | Mateus Dias Quinaz | |
| 2017/0222576 A1 | 8/2017 | Majidi et al. | |
| 2018/0143687 A1 | 5/2018 | Moessinger et al. | |
| 2018/0179051 A1* | 6/2018 | Keller | G06F 3/016 |
| 2018/0181202 A1* | 6/2018 | Khoshkava | G06F 3/04166 |

OTHER PUBLICATIONS

International Search Report for PCT/IB2018/055075, dated Mar. 8, 2019, 4 pages.
Written Opinion of the ISA for PCT/IB2018/055075, dated Mar. 8, 2019, 9 pages.

\* cited by examiner

*Primary Examiner* — Carl Adams
(74) *Attorney, Agent, or Firm* — Nixon & Vanderhye P.C.

(57) ABSTRACT

The present disclosure relates to a device including electrostatic brakes providing haptic kinaesthetic feedback to a user in e.g. assistive, rehabilitation or virtual reality scenarios, as well as tele-manipulation.

17 Claims, 6 Drawing Sheets

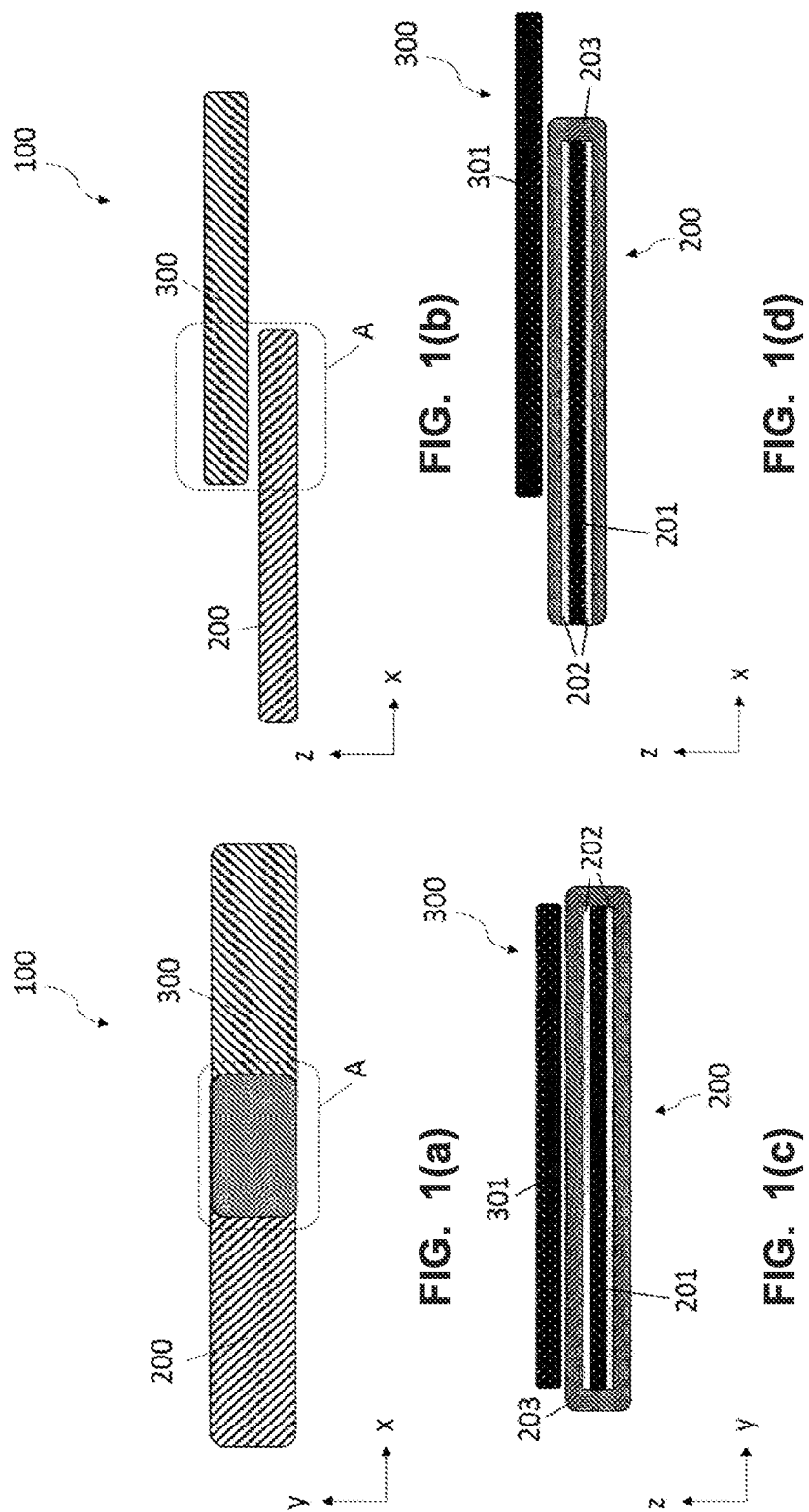

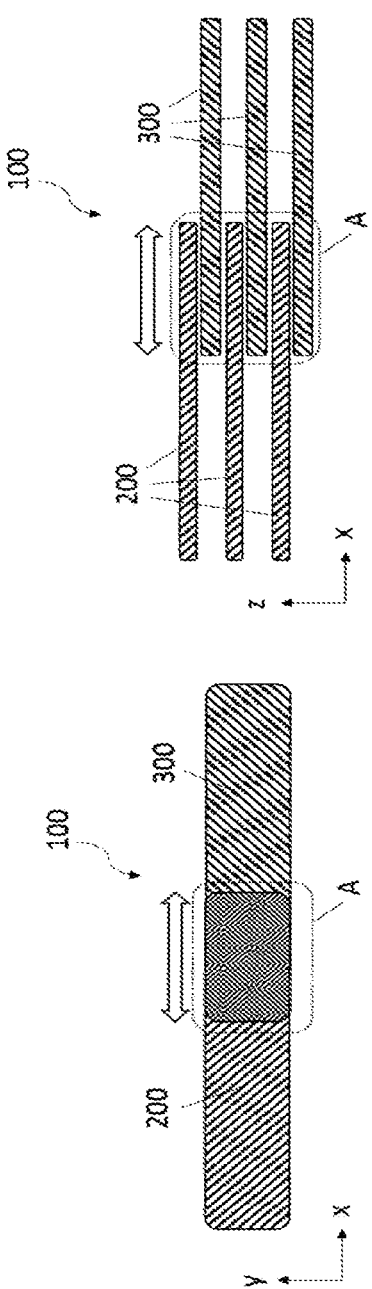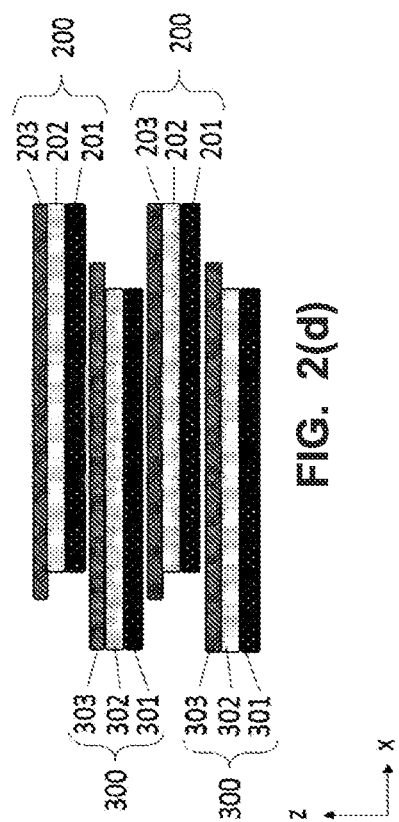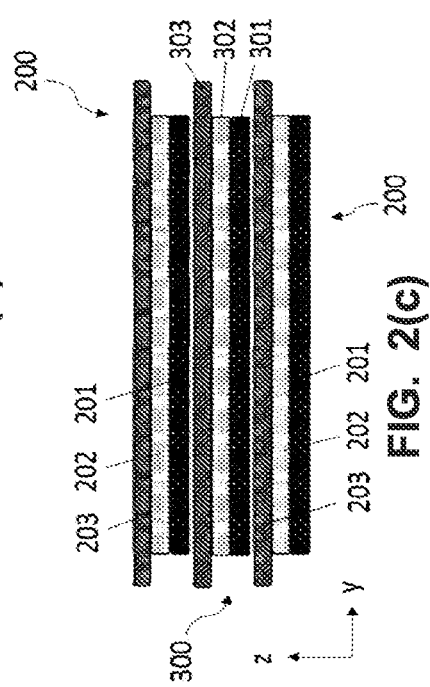

ELECTROSTATIC BRAKE-BASED HAPTIC DEVICE

This application is the U.S. national phase of International Application No. PCT/IB2018/055075 filed 10 Jul. 2018, which designated the U.S., the entire contents of which is hereby incorporated by reference.

TECHNICAL FIELD

The present disclosure belongs to the field of exoskeleton devices. In particular, the present disclosure relates to a device including electrostatic brakes providing haptic kinaesthetic feedback to a user in e.g. assistive, rehabilitation or virtual reality scenarios, as well as tele-manipulation.

BACKGROUND ART

Augmented Reality (AR) and Virtual Reality (VR) associated with Wearable Electronics and Computing enable novel means of interacting with people, machines, and data. Although impressive and rapid progresses have been made for visual display technologies (such as the HoloLens AR or the Oculus Rift VR), other senses have been explored far less rigorously. In particular, the sense of touch is highly developed in humans and is crucial in interacting with our environment. Thus, creating small and light actuators to generate haptic feedback and allow our body to interact with virtual objects is becoming an important objective.

The perceptual mechanisms behind the experience of holding an object or exploring the shape and texture of its surface are complex and still under investigation. However, haptic literature discerns kinaesthetic and cutaneous components. The kinaesthetic feedback requires large actuation forces and provides the user with information about the relative position of the parts of his body (e.g., moving entire finger, or exerting force on joints). Large forces and motion blocking have been rendered in VR with a relatively high fidelity using actuated articulated arms, akin to an exoskeleton. However, they are typically bulky and require complex mechanical setups. They restrict the freedom of movement, depend upon heavy user instrumentation and are typically restricted to lab environments or specialized working areas because they are not adapted to mobile use. Large forces can also be rendered to the hand via the use of glove-based exoskeletons, which use bulky tendon actuators routed to the fingertips via the exoskeleton to provide force feedback to each finger. However, the required large instrumentation is not desirable in many settings and situations.

In this context, two main technologies used in the prior art can be distinguished: the first are pneumatic based; the second are motor-based. Pneumatic-driven haptic feedback gloves use pistons connected to an exoskeleton to block and control (with complex big pumps) fingers' positions. Electrically driven gloves using motors linked to cables or articulations on an exoskeleton are slightly smaller but still complex, bulky and fragile.

A third approach is to use a brake, which can be active or passive. Actuators have been recently developed and proposed for various applications such as a passive, spring based, force feedback device for fingers force feedback. An active, vacuum based, brake using simple interdigitated strips for vehicle applications (seat belt, whiplash protection, etc . . . ) has been developed, using vacuum to pull plates together and thus control friction and hence braking force.

Beside VR haptic devices, several concepts of hand exoskeletons for motor rehabilitation and assistance purposes have been proposed in the past. Where a person's gripping movement with a hand does not have sufficient force, such a gripping movement may be found to be impossible or almost impossible to execute. Examples of cases where muscular strength is not sufficient for such gripping movements include elderly persons with muscle weakening and persons being rehabilitated after, for example, brain injury. The same problem may also affect persons who have certain types of chronic conditions, e.g. rheumatism. Other examples of situations where it may be advantageous or necessary for persons to increase the muscular force which the hand can apply to an object in a gripping movement include, for example, astronauts or manual workers in certain situations.

US Patent Application 2016/0361179 discloses a device for actively and dynamically assist and lock joints, with low power consumption, small volume and light weight, having a supporting structure in the joint, at least one tensioning system fixed to the supporting structure and at least one artificial tendon connected to the tensioning system. The tension system interacts with the locking system in order to assist the user's joints when needed.

US Patent Application 2016/0015590 discloses a hand exoskeleton device that can be mounted onto a human body, and can operate a three-layered sliding spring mechanism serving as a motion transfer mechanism for applying drive power to a distal interphalangeal joint (DIP joint), a proximal interphalangeal joint (PIP joint) and a metacarpophalangeal joint (MP joint) using a single direct acting actuator, thereby supporting the gripping motions of the human body with the device mounted thereon.

US Patent Application 2013/0219585 discloses a grasp assist system including a glove, actuator assembly, and controller. The glove includes a digit, i.e., a finger or thumb, and a force sensor. The sensor measures a grasping force applied to an object by an operator wearing the glove. Phalange rings are positioned with respect to the digit. A flexible tendon is connected at one end to one of the rings and is routed through the remaining rings. An exoskeleton positioned with respect to the digit includes hinged interconnecting members each connected to a corresponding ring, and/or a single piece of slotted material. The actuator assembly is connected to another end of the tendon. The controller calculates a tensile force in response to the measured grasping force, and commands the tensile force from the actuator assembly to thereby pull on the tendon. The exoskeleton offloads some of the tensile force from the operator's finger to the glove.

US Patent Application 2013/0072829 discloses a flexible, modular and lightweight hand rehabilitation device comprising a brace fitted to partially cover the patient's hand and forearm, the device comprising, all placed on the back of the hand with the palm totally free, flexible rods for a passive and assisted active bending/extension of the five fingers, finger gloves provided with thimbles, fixed rods or plates stabilised to thimbles and hinged to one end of the flexible rods by means of a hinge and a quick coupling mechanism defining an articulated joint, a movement/command and control unit integral to the brace or remotely located relative to the same and provided with five actuating means for moving the flexible rods and further comprising means for adjusting the tension of said rods, means for adjusting and adapting the rehabilitation device to the hand's anatomical features and a control and management software.

US Patent Application 2010/0041521 discloses a finger glove for use in gripping movements with one or more fingers of a human hand enclosed in the glove. The glove includes glove fingers and a palm. At least one glove finger is adapted to include on each side an artificial tendon that extends along an inside of the glove. A yoke is fitted in a tip of the at least one glove finger and intended to surround a tip of an enclosed finger. At each side of the glove finger artificial tendons are connected to the yoke. A system including the finger glove having a force detecting sensor is situated on the inside of the at least one glove finger and is adapted to detect a force between a finger enclosed in the glove finger and a contact surface applied to the finger. The artificial tendons for a glove finger are connected to at least one actuator and a control unit adapted to cause the at least one actuator to exert a pulling force on the artificial tendons of the glove finger based on a force detected in the force detecting sensor, whereby the finger enclosed in the glove finger is caused to bend.

Electrostatic clutch for robotic and exoskeleton (walking) applications have been reported in US Patent Application 2017/0222576.

All the above-mentioned systems, such as hand exoskeletons, present certain drawbacks or otherwise limitations. For instance, many of those devices are bulky, poorly usable and costly in view of their complexity. Some are not designed to be used outside of clinical settings and/or without any monitoring performed by a medical practitioner mainly because of their non-portability. Moreover, none of the above systems are conceived and/or optimized to provide a kinaesthetic haptic feedback to a user.

SUMMARY OF INVENTION

The subject-matter described in the present application relates to devices, systems and methods to efficiently, rapidly, and reversibly block or at least hamper the movement of a body portion, such as for instance body articulations. The device according to some embodiments is small, lightweight and conformable to the body of a user while being able to generate a force capable to totally block a body portion's position, or at least hamper its movements, on demand. In some embodiments, the device is suitable for being used or embedded into apparatuses such as body suits or gloves e.g. for grasping assistance (in case of hand-tailored devices) and/or for providing an active haptic feedback, particularly a kinaesthetic one, depending on the needs and circumstances.

According to one object and embodiment of the present invention, it is therefore provided a device comprising:

an electrostatic brake configured to be mounted on the body of a user, said brake comprising i) a first electrode comprising a conductive and flexible film, wherein a surface of the first electrode is coated with a dielectric material to cover the conductive film;

ii) a first frame affixed to an end of the first electrode;

iii) a second electrode comprising a conductive and flexible film, wherein a surface of the second electrode is aligned parallel to the surface of the first electrode so that the first and the second electrodes partially overlap;

iv) a second frame affixed to an end of the second electrode; and v) means for coupling said first and second electrodes so to allow them to move linearly relative to each other while keeping a partial overlap of their surfaces and a power source for applying a voltage between the first electrode and the second electrode to develop an electrostatic charge, in such a way as to generate an attractive force between said first and second electrodes and reversibly increase the sliding friction between the electrodes, characterized in that said first frame, second frame and coupling means are devoid of any tensioner or spring elements.

Another object and embodiment of the present disclosure relates to the use of the device of the invention in a virtual or augmented reality application.

A further object and embodiment of the present disclosure relates to a system for providing a kinaesthetic haptic feedback on the body of a user in a virtual or augmented reality application, said system comprising the device of the invention and at least one of a position sensor, a force sensor and a touch sensor.

Still a further object and embodiment of the present disclosure relates to a method for providing a kinaesthetic haptic feedback on the body of a user, said method comprising a step of actuating an electrostatic brake placed on the body of said user in a way as to at least hamper the movement of a body part.

Still a further object and embodiment of the present disclosure relates to a method for providing assisted grasping to a user, said method comprising a step of actuating an electrostatic brake placed on a finger or a hand of said user in a way as to block the movement of a finger and/or a hand in a certain position.

The above and other objects, embodiments, features and advantages of the herein presented subject-matter will become more apparent from a study of the following description with reference to the attached figures.

BRIEF DESCRIPTION OF DRAWINGS

In the Figures:

FIG. 1 depicts one embodiment of the device of the invention: a) top view; b) lateral view; c) cut view; d) detailed lateral view;

FIG. 2 depicts another embodiment of the device of the invention with a multi-stack configuration: a) top view; b) lateral view; c) cut view; d) detailed lateral view;

DETAILED DESCRIPTION OF THE INVENTION

Figure 3A:
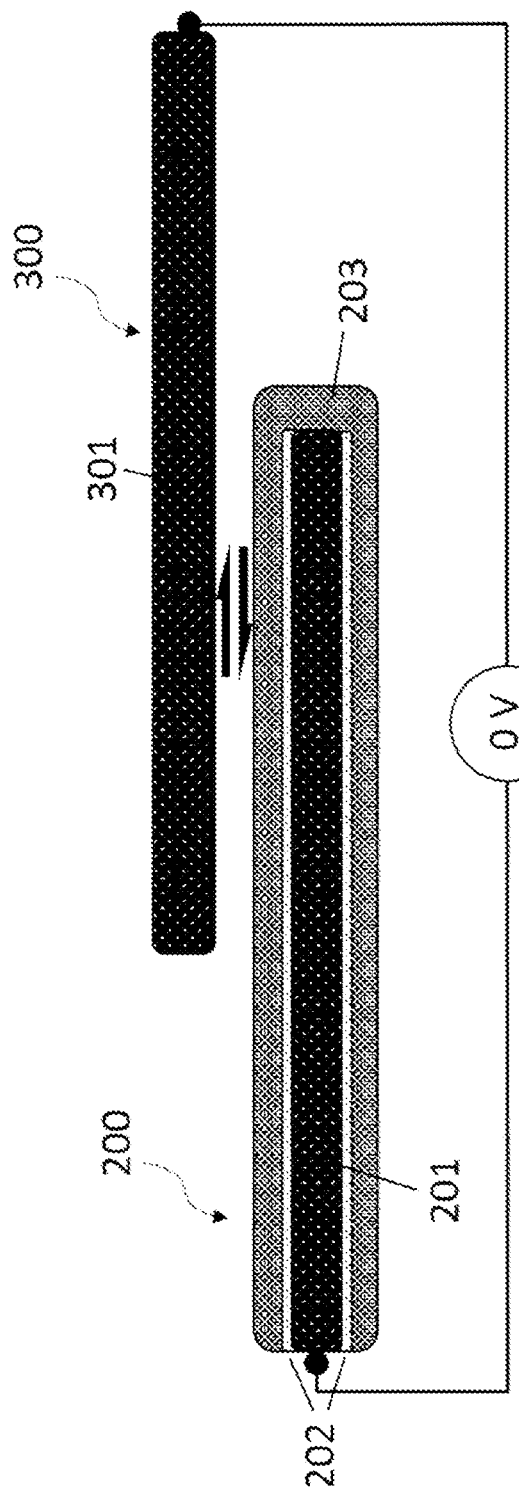
FIG. 3 depicts one embodiment of the device of the invention in operation without any applied voltage (a) and with an applied voltage (b)

As used herein and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes"

and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

Unless defined otherwise, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated.

The present disclosure will be better understood with the help of the following definitions.

As used in the present disclosure, "haptic technology" or "haptics" is a feedback technology which recreates or stimulates the sense of touch by applying forces, pressures, vibrations and/or motions to the user. This mechanical stimulation can be used for instance to assist in the creation of virtual objects in a computer simulation, to control such virtual objects, and to enhance the remote control of machines and devices (telerobotics). A "haptic device" is a device that exploits haptic technology. Haptic devices may incorporate sensors that measure forces, pressures, position, strain, or movements exerted by the user on an interface and vice versa. Haptic technology has made it possible to investigate how the human sense of touch works by allowing the creation of carefully controlled haptic virtual objects. These objects are used to systematically probe human haptic capabilities, which would otherwise be difficult to achieve. The most common applications of the haptic technology include the provision of haptic feedbacks for controllers such as game controllers, joysticks, remote-controlled robotic tools, mobile devices such as mobile phones, virtual reality systems and so forth. Haptic interfaces for medical simulation may prove especially useful for e.g. training in minimally invasive procedures, as well as for performing remote surgery.

The human sense of touch can be divided into two separate channels. Kinaesthetic perception refers to the sensations of positions, velocities, forces and constraints that arise from the muscles and tendons. Kinaesthetic feedback is based on larger scale forces transmitted through the joints and muscles which inform us of relative limb and finger positions through the sense of proprioception. Force-feedback devices appeal to the kinaesthetic senses by presenting computer-controlled forces to create the illusion of contact with a rigid surface. Cutaneous stimuli are felt by the pressure receptors in the skin, typically in the fingertips, providing information on texture, shape, and force direction during object manipulation. The cutaneous class of sensations arise through direct contact with the skin surface. Cutaneous stimulation can be further separated into the sensations of pressure, stretch, vibration, and temperature. Tactile devices generally appeal to the cutaneous senses by skin indentation, vibration, stretch and/or electrical stimulation. The device of the present invention is construed and assembled in order to provide a tactile feedback involving kinaesthetic sensations. However, in some embodiments according to the present invention, a tactile feedback involving both kinaesthetic and cutaneous sensations can be envisaged.

The wording "assisted grasping" or "assisted grasp" refers to the capability of certain embodiments of the device of the invention to either help and support the grasping ability, augment the grasping force or maintain the grasping force of a user wearing the device. For example, manual operations requiring a repetitive or sustained grasping of an object can stress a user's hands, fingers and forearms. As a result, a user's grasp strength and productivity can gradually decline over the course of a certain task. Grasp strength can also vary widely between different users due to differences in physical stature, injury, and/or muscle fatigue. The variable nature of a given user's grasp strength may result in relatively inefficient execution of certain grasp-related tasks or works. Conventional devices such as wrist straps and braces exist for easing some of the stress on an operator, although such devices may remain less than optimal for improving overall grasp strength.

In the frame of the present invention, an "electrostatic brake", also referred to herein as "electroadhesive brake", "electrostatic clutch" or "electroadhesive clutch", is an active device exploiting electro-attractive forces exerted between two conductive elements upon application of a voltage to operate a partial or complete reciprocal blockage of said conductive elements via frictional forces.

The expression "film electrode" relates to the thin form factor of the electrodes according to the present invention. Generally speaking, a "film" as used herein relates to a layer of a material having a thickness much smaller than the other dimensions, e.g. at least one fifth compared to the other dimensions. Typically, a film is a solid layer having an upper surface and a bottom surface, with any suitable shape, and a thickness generally in the order of nanometers, micrometers or even millimetres, depending on the needs and circumstances, e.g. the manufacturing steps used to produce it.

The term "flexible", as used herein, designates the capacity of a film electrode according to the invention to actively or passively bend in one or more off-axis directions, preferably perpendicularly compared the long axis of said electrode, according a the movement of a user's body part, such as a hand or a finger, it is connected with. Particularly, the term flexible is herein used to designate the capacity of a film electrode according to the invention to reversibly and elastically bend, that is, the bending is such that the film electrode regains its initial shape upon ending of a bending or loading force.

A "dielectric", or "dielectric material", is an electrical insulator that can be highly polarized by an applied electric field.

The present disclosure, as described hereinafter, describes a simple and elegant solution to tackle and overcome the shortcomings of known wearable electronic-haptic-devices. Furthermore, it describes an assisted grasping device useful in several different work contexts as well as for rehabilitative/supportive purposes vis-à-vis mobility-impaired people.

The device is directly controlled by an electronic circuit enabling an easy control and very fast actuation. The device as described in the present disclosure comprises, in one aspect, several interdigitated thin flexible metal strips, each covered by a dielectric coating (or dielectric coating+an adhesive). When unpowered, the whole device is flexible and stretchable, conforming to a user's body part shape, such as a finger's shape. Of course, other body parts may be envisaged, such as an arm or a leg, or parts of them and the functions of the present invention applied to them. The strips are connected to two electrical terminals and form a capacitance. Applying a voltage between the terminals charges the capacitance and generates an attractive electrostatic force between the strips. The attractive force squeezes the strips together, which greatly increases their friction and thus blocks their relative movement, preventing or at least hampering a body part of a user wearing the device from moving. By turning off the voltage, the electrostatic attraction is removed, thus releasing the strips, allowing them to slide freely and hence allowing the body part to move freely once again.

As the device has been imagined and developed for being simple, lightweight and compliant to body joints' movements (particularly hands and fingers), a key feature relies in the alignment means used for the electrodes, as well as in the form factor, materials and intrinsic flexibility of these latter: thanks to these characteristics, the device in embodiments is completely devoid of any tensioner or spring element such as for instance springs, elastic, rigid or semi-rigid bands or strips, belts, ribbons and the like, connecting the frames and the electrodes between them, in any combination (i.e. electrodes between them, frames between them and/or electrodes-frames between them). This further facilitates the manufacturing process and the force distribution along the clutch upon bending of the electrodes.

With reference to FIGS. 1 and 2, one exemplary, non-limiting embodiment of, respectively, the electrostatic brake 100 and the entire device of the invention, is shown. As shown in FIG. 1, the electrostatic brake 100, in its simplest embodiment, comprises two thin-form electrodes designated for the sake of simplicity in FIGS. 1a) and 1b) 200 and 300. FIG. 1c) and 1d) depict a more detailed illustration of the same electrodes 200 and 300.

A first electrode 200 comprises a conductive and flexible film 201 having at least one surface thereof coated with a dielectric material 203 to cover it. The coating can be performed by any suitable means known in the art such as for instance growing, gluing, spraying, sputtering, casting, pouring, chemical or physical deposition and the like. In the embodiment shown on FIGS. 1 and 2, an adhesive layer 202 is used to glue the dielectric material 203 to the conductive film 201. Using a conductive adhesive layer 202 to attach the dielectric material 203 to the conductive film 201 can provide the advantage of reducing the driving voltage, as the adhesive 202 results as part of the conductive element rather than being part of the dielectric one.

The electrostatic brake 100 further features a second electrode 300 comprising a conductive and flexible film 301 having a surface aligned parallel to the surface of the first electrode 200 so that said first and the second electrodes 200, 300 partially overlap over an overlap area A. The overlap area A between the surfaces of the first and the second electrodes 200, 300 is comprised between 10% and 100%, such as for instance 20, 30, 40, 50, 60, 70, 80 or 90%. In one embodiment, the overlap area A is comprised between 30 and 90%, such as between 40 and 80%. The length of the electrodes 200, 300 can vary from few centimeters to 1 meter, such as 20, 30 or 50 cm each, and the length of the electrodes is not limiting as long as an overlap area A as herein described is kept in place.

In some embodiments, the film electrodes 200 according to the invention have a thickness comprised between 1 µm and 5 mm, such as between 5 µm and 5 mm, between 5 µm and 1 mm, between 10 µm and 1 mm, between 5 µm and 500 µm, between 50 µm and 500 µm between, between 50 µm and 150 µm, 100 µm and 500 µm or between 200 µm and 500 µm.

In some embodiments, the conductive films 201, 301 comprise conductive materials such as metals, including alloys or oxides thereof, including copper, iron, gold, platinum, silver and the like, preferably stainless steel, nickel or aluminium; conductive textiles; composite materials made with any combination of polymeric and conductive materials such as for instance metallic particles-, flakes- or fibers-filled polymers, as well as metal-coated polymers.

In some embodiments, the dielectric material layer 203 according to the invention has a thickness comprised between 100 nm and 1 mm, such as between 500 nm and 1 mm, between 500 nm and 500 µm, between 1 µm and 100 µm, between 1 µm and 50 µm, between 5 µm and 15 µm, between 500 nm and 5 µm, 1 µm and 5 µm or between 500 nm and 1 µm. In a specific embodiment, the dielectric material layer 203 has a thickness comprised between 500 nm and 50 µm. Some preferred dielectric materials according to the invention are high-permittivity materials such as polymide, Poly(vinylidene fluoride)-triflouorethylene-chlorotrifluoroethylene polymers (PVDF-TrFE-CTFE), Poly(vinylidene fluoride)-triflouorethylene-chlorofluoroethylene polymers (PVDF-TrFE-CFE), BaTiO3 and Lead zirconate titanate (PZT) and their composites; acrylonitrile butadiene styrene (ABS), poly ethylene (PE), poly propylene (PP), rubbers, polyesthers, epoxys or combinations thereof.

Figure 4:
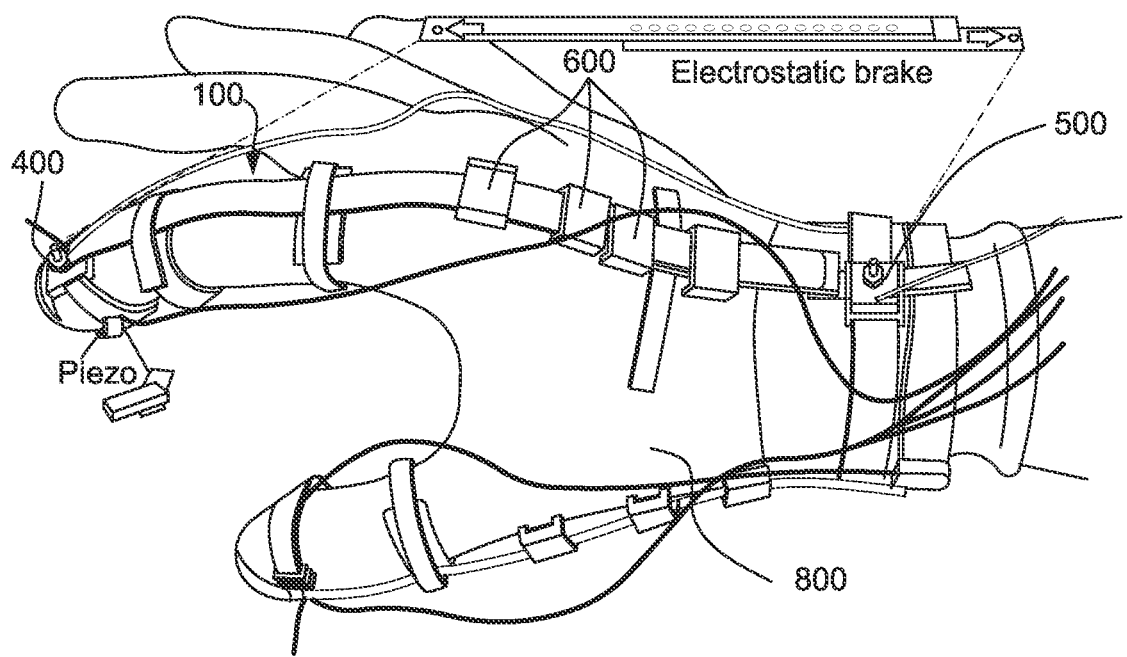
FIG. 4 shows a photograph of a real, implemented embodiment of the device of the invention for providing kinaesthetic haptic sensations to a hand and fingers of a user, the device being operatively coupled with a glove.
Figure 5A:
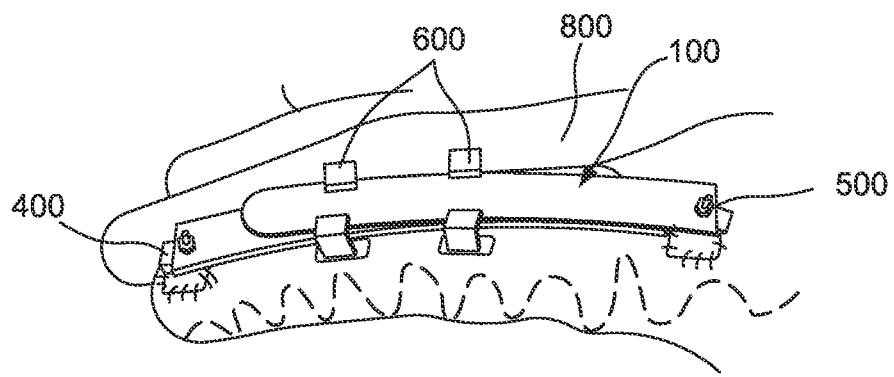
FIGS. 5(a) to 5(c) shows photographs of an alternative real, implemented embodiment of the device of the invention for providing kinaesthetic haptic sensations to a hand and fingers of a user, the device being operatively connected with a glove in perspective view (FIG. 5(a)), top view (FIG. 5(b)) and side view (FIG. 5(c))
Figure 5B:
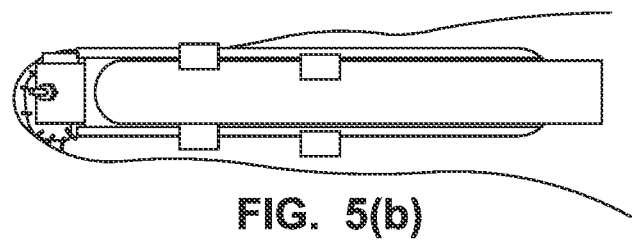
Figure 5C:
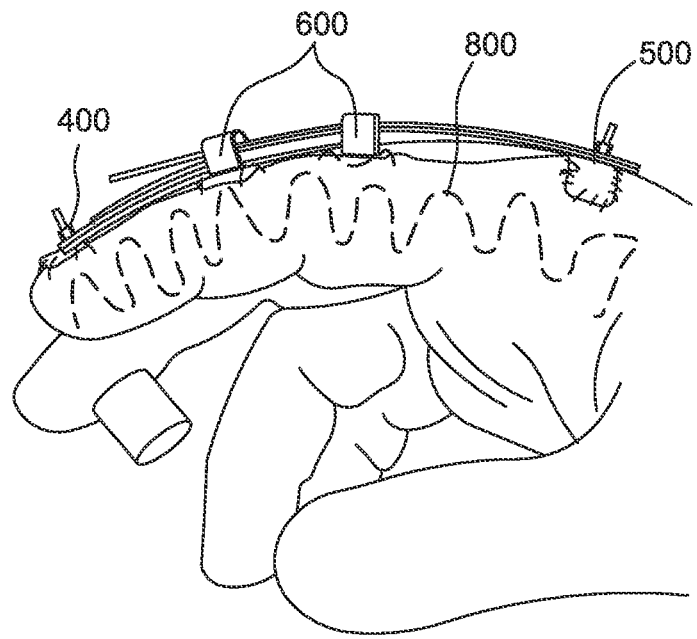

The device further comprises a first frame 400 affixed to an end of the first electrode 200 and a second frame 500 affixed to an end of the second electrode 300 (FIGS. 4 and 5). Those frames are needed to connect the electrostatic brake 100 to a body part of a user, and actually work as means for fixation of the brake 100 to a user. For instance, frames 400, 500 can be embodied as braces, laces, bands, rings or straps, possibly having hooks-and-loops or side-release buckles to better adjust the device on a user's body part. Electrodes 200, 300 are coupled to frames 400, 500, respectively, with any means known in the art, like as sewing, gluing, soldering and so forth.

Electrodes 200, 300 are physically connected between them by means 600 for coupling them, configured so to allow said electrodes 200, 300 to move linearly relative to each other while keeping a partial overlap A of their surfaces (FIGS. 4 and 5). Typically, means 600 comprises or consists in one (or a plurality of) guide(s) such as 3D printed plastic guide(s) designed to allocate electrodes 200, 300 into a bore or cavity of said guides 600, so to permit a longitudinal relative displacement compared to the longer axis of the electrodes in the absence of any driving voltage. However, any type of guide 600 can be envisaged, as long as electrodes 200, 300 are free to move longitudinally in the absence of a voltage while keeping a partial overlap area A, and provided that said means 600 are not tensioners or spring elements.

The device of the invention further features a power supply 700 for applying a voltage across the first and the second electrodes 200, 300 to develop an electrostatic charge, in such a way as to generate an attractive force between said first and second electrodes 200, 300 and reversibly increase the friction between the electrodes. In the vast majority of the applications of the device of the invention, the voltage is comprised between 20 and 5000 Volts, such as 100, 200, 500, 1000, 2000, 3000, 4000 Volts. In one embodiment, the voltage is comprised between 500 and 3000 Volts. In another embodiment, the voltage is 2000 Volts. Alternating current (AC) or direct current (DC) can be provided, with AC having the further advantage at high voltages of limiting of even eliminating charge injection in the dielectric layers, thus allowing the electrostatic force to be turned off as soon as the voltage is reduced.

In the majority of the embodiments of the invention, the configurations in terms of size and thickness of the elements of the electrostatic brake 100, as well as the applied voltage, allows to generate a friction force between the first and the second electrodes 200, 300 typically comprised between 2 and 200 Newtons, such as 2, 5, 10, 20, 30, 40, 50, 100, 150 or 200 Newtons.

With reference to FIG. 2, a multi-layered stack of electrodes 200, 300 is depicted. Said stack is configured to provide higher total frictional forces between the electrodes and more tailored control over the distribution of the same frictional forces, as different dielectric and electrodes can be used in a stack, and as any combination of voltage application across the electrodes of the brake can be envisaged. In said configuration, each one of the first electrodes 200 comprise a conductive film 201, an adhesive layer 202 and a dielectric layer 203, and each one of the second electrodes 300 comprise a conductive film 301, an adhesive layer 302 and a dielectric layer 303.

Figure 3B:
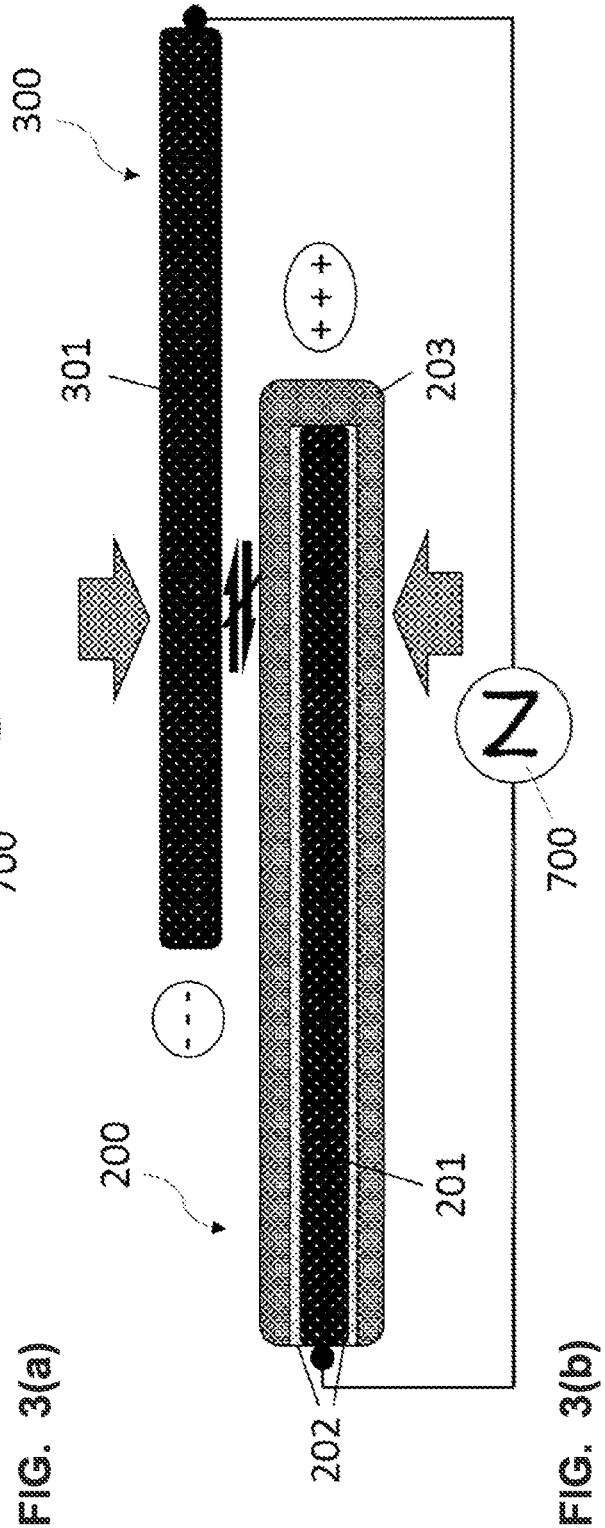

FIG. 3 depicts one embodiment of the device of the invention in operation. When the voltage difference between the electrodes 200, 300 is zero, they freely slide with a very low friction, enabling full and unimpeded movements (FIG. 3a). When a voltage is applied between the strips, an attractive electrostatic force is generated between the electrodes 200, 300, pulling them together (FIG. 3b). The electrically-controlled normal force leads to frictional forces between the electrodes 200, 300, partially or fully blocking the movement of the electrostatic brake: the higher the applied voltage, the higher the friction force. This principle is of course applicable to all embodiments of the invention, for example as illustrated in FIGS. 2(a) to 2(d), but not limited to these embodiments.

As said, the device can be used in different contexts and situations. For instance, it can be used for providing a kinaesthetic haptic feedback on the body or a body part of a user, such as for instance joints (including wrists, ankles, knees, elbows or fingers), hands, feet, back, neck, hips or face of a user. This is of particular interest in scenarios such as rehabilitative therapies or virtual/augmented reality, where kinaesthetic haptic feedback can be used to perceive objects in a virtual space or to accelerate recovery of body sensations after an injury or disease (e.g. a stroke). In this perspective, the device can be embodied in several ways: for instance, body haptic suits, braces, splints or gloves can be instrumented with the device of the invention to provide haptic sensations to a user. Furthermore, more than one device can be included in e.g. a garment to finely tune the perceivable sensations on different or the same body parts.

Figure 6:
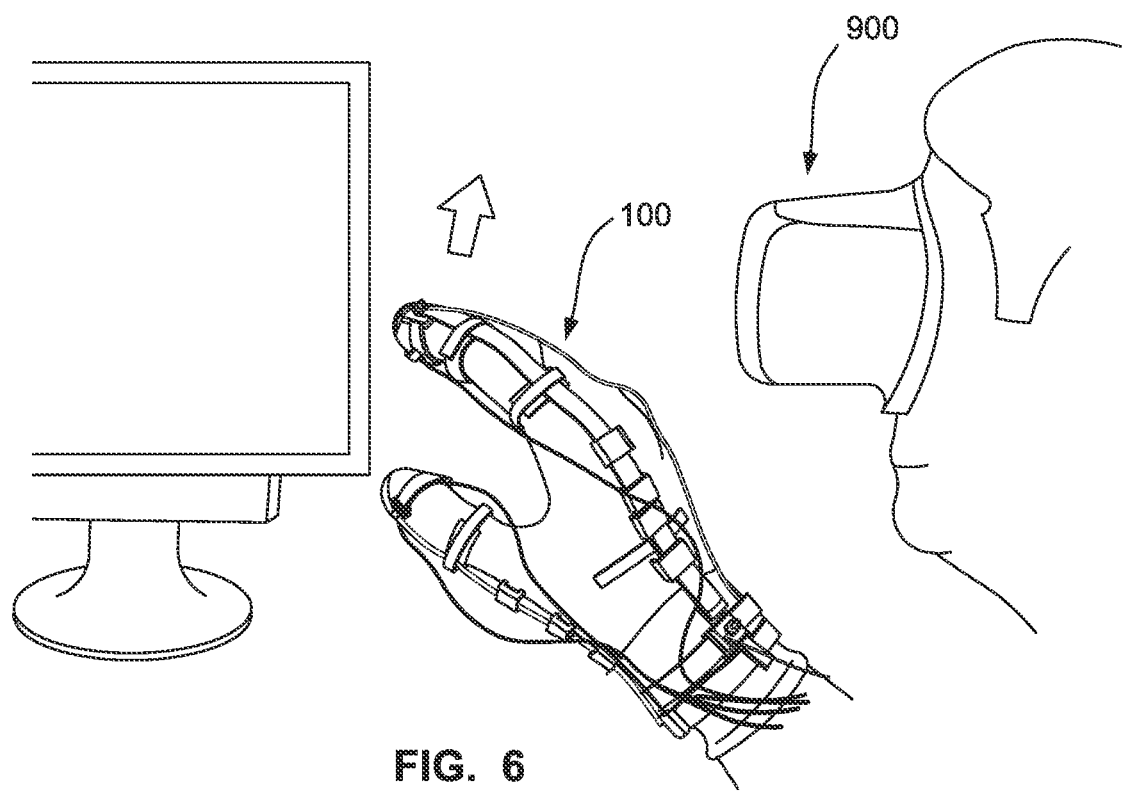
FIG. 6 shows a photograph of an embodiment of the system according to the present invention: a user wears the device of the invention and a virtual reality headset for displaying a virtual scene or object to said user.

According to one object of the invention, the subject matter of the present disclosure further relates to the use of the device of the invention in a virtual or augmented reality (VR/AR) application. To this aim, still a further object of the present disclosure relates to a system for providing a kinaesthetic haptic feedback on the body of a user in a virtual or augmented reality application, said system comprising the device of the invention and one of a position sensor, a force sensor and a touch sensor. In the frame of virtual or augmented reality, the system typically foresees in some aspects the device of the invention embodied as, or embedded into, a tool or a garment such as body suits, braces, splints or gloves, and operatively connected with additional elements such as one or a plurality of position sensors, force sensors, touch sensors of combinations of the foregoing. As it will be evident to a person skilled in the art, elements such as temperature or tactile feedback devices can be operatively coupled with the device and/or the system of the invention to provide more immersive and realistic sensations to a user. The system can additionally include means 900 for displaying a virtual scene or object to a user in an all-in-one setting; said means can be for instance goggles, virtual reality headsets or video screens or other equivalent devices (illustrated in FIG. 6).

In the particular case of a glove 800 integrating the device of the invention on one or more fingers (preferably at least two fingers), as well as on the entire hand including one or more fingers, this can allow simulating the feel of solid object: when a user grabs a virtual object, he feels that is solid, though it of course does not exist. The finger clutch can be combined with other actuators to form a soft, flexible and programmable glove to provide a rich haptic feedback to the hand, without requiring excessive external machinery, thus overcoming many of the limitations of current virtual or augmented feedback devices. Compared to devices known in the art, the present invention is extremely compact, has a faster reaction speed (few milliseconds), has a small size, is fully flexible, stretchable and conformable to finger's shape and is directly controlled electrically by a simple electrical circuit and a computer. All these advantages enable using a user's fingers to feel and interact precisely with virtual worlds in a very natural manner: no complex bulky external robotic parts to strap on and no hand controllers are needed. The potential application of such gloves are numerous, from consumer electronics, by providing new haptic sensations (e.g. for gaming and movies), to tele-operation and remote surgery, to cite some.

For what said above, it is clearly another object of the present invention to provide for a method for providing a kinaesthetic haptic feedback on the body of a user, such as a finger or a hand, said method comprising a step of actuating an electrostatic brake placed on the body of said user in a way as to at least hamper the movement of a body part.

Related to the above, it is another object of the present invention to provide for a method for providing assisted grasping to a user, said method comprising a step of actuating an electrostatic brake placed on a finger or a hand of said user in a way as to block the movement of a finger and/or a hand in a certain position.

Some Examples will be hereinafter presented, which however are not to be considered as limiting of the disclosed matter.

EXAMPLES

The ability to grasp objects is amongst the most useful skills we can perform in VR. One challenging aspect in supporting grasping in VR is the wide array of possible grasps which require the fingers to be free to move into different configurations. Traditionally, grasping feedback in VR has been supported via glove-based exoskeletons which create braking forces on the fingers, render localized tactile feedback on the fingertips, or combine aspects of both. These devices often employ complex mechanisms around the hand which may either add weight, constrain the movement of the fingers, or both. As a result, the full range of interaction capabilities of the human hand are under-utilized.

To address this challenge, the inventors introduced a finger-mounted haptic mechanism capable of achieving up to 20N of holding force on each finger when flexing inward.

This novel approach is based on electrostatic attraction to create a rapidly controlled braking force between two electrically charged strips of metal. Inventors harnessed the resulting braking force to rapidly render on-demand kinaesthetic feedback which blocks the motion of the fingers. Crucially, this allow for the design of a very thin and flexible form factor haptic interface for grasping objects in VR—a long standing goal which has thus far relied on space inefficient bulky mechanisms. Such an interface may also be generalized to function beyond VR, for example in Augmented Reality (AR), robotic tele-operation, and rehabilitation applications.

In contrast to a one-size-fits-all mounting solution, the device was integrated onto the index finger and thumb using modular fittings with different strip lengths inserted into 3D printed articulated guides to keep them moving smoothly. The strips are anchored onto the fingertip and wrist resulting in frictional forces due to sliding when the finger is flexed. This mounting strategy allows for easy adaptation to different hand sizes.

The control electronics provide up to 1500V to the strips and are connected via a 1.5 m long cable attached at the wrist. The resulting integration into VR allows freedom of movement for both the fingers and hand. The volume of the control electronics can be reduced to a few cm³ with off-the shelf components, and the very low power consumption (less than 100 mW) allows for battery powered operation, providing a straightforward path to widespread real-world implementation.

Operation Principle

At the heart of the used approach is a laminar electrostatic (ES) brake. The ES brake consists of 18 cm long thin flexible metal strips that slide freely when no control voltage is applied, but generate up to 20 N of holding force per pair of strips when a suitable control voltage is applied. One of the key features of the ES brake is its thin form-factor, ideal for wearable applications. The active part of the brake is conformable to fingers and can be directly mounted or inserted on a glove. The brake mass on the glove is only 8 g, and it is only 6 mm high (including attachments).

As shown in FIGS. 4 and 5, the ES brake is attached to the glove, covering the back of the hand and the back of the finger. The high degree of flexibility allows excellent conformity to any hand shape. Each brake element consist of two 100 μm thick steel strips, separated by a thin insulation layer bonded to one strip, forming a capacitor $C_{strip}$:

$$C_{strip} = \frac{\epsilon_r \epsilon_0 A}{d}$$

where $\epsilon_r$ is the relative permitivity of the insulator between the electrodes, $\epsilon_0$ is the permittivity of vacuum, A is the overlap area between the electrodes, and d is the thin dielectric gap between the electrodes. One strip (the "hand strip") is attached via the glove to a fixed point on the back of the hand, while the other strip (the "finger strip" is attached via the glove to a fingertip. When the voltage difference between the strips is zero, the strips freely slide with a very low friction, enabling full and unimpeded finger movements (FIG. 3a). When a voltage is applied between the strips, an attractive electrostatic force $F_{compression}$ is generated between the strips, pulling them together (FIG. 3b):

$$F_{compression} = \frac{\epsilon_r \epsilon_0 A V^2}{2d^2}$$

where V is the voltage applied between the electrodes. This electrically-controlled normal force leads to frictional forces between the strips, partially or fully blocking the movement of the finger. The friction force is less than or equal to the friction coefficient μ times $F_{compression}$:

$$F_{friction} \leq \mu F_{compression}$$

The higher the applied voltage, the higher the friction force. Using this ES brake, we can thus apply a high blocking force to the fingers, providing kinaesthetic haptic feedback. The power consumption $P_{ESbrake}$ of the brake is determined by the energy to charge the capacitor multiplied by the switching frequency f:

$$P_{ESbrake} = \frac{E}{t} = \frac{1}{2} C V^2 f$$

Operating at 20 Hz and 1.5 kV, the device does not heat up when turned on as power consumption is less than 60 mW.

Fabrication of the ES Brake

Stainless steel was chosen as conductor since it is a reliable spring material. The bending stiffness of a strip scales approximately with the cube of the shim thickness. One must find a suitable compromise between being thick enough for the shim to slide easily without buckling or plastically deforming, yet thin enough so that the force to bend the strip is low enough to be nearly imperceptible.

The fabrication of the ES brake strips consists of 3 steps: first, two strips 18 cm long and 1 cm wide were laser cut from 100 μm thick stainless steel sheets. Strips are shortened at a later time to fit the user's hand and fingers. Second, after annealing the strips and polishing the edges, it is deposited on the top surface of the "hand strip" a 32 μm thick conductive double-side adhesive and a 13 μm thin polyimide film, slightly wider than the steel shim to avoid short circuits. Polyimide has a high breakdown field of over 300 V/μm. Using a conductive adhesive to attach the polyimide to the steel was a key step in reducing the driving voltage, as the adhesive is thus part of the electrode rather than being part of the dielectric. The fabrication process is straightforward, low-cost and readily industrialized.

Control Electronics for ES Brake

To actuate and control the ES brake, a custom high voltage (HV) power source supplying 2000 V at 500 μA in DC and square-wave AC at a switching frequency of up to 1 kHz was assembled. The HV supply is based on a DC-DC converter (XP Power, EMCO 2 kV) with maximum power of 1 W, with the current limited for safety reasons. The AC signal is generated from the DC voltage using opto couplers (MPI Technologies). This HVS was controlled by an Arduino micro controller via a USB connection to a laptop. For a fully portable application, the electronics could be scaled down to a few cm3.

Bipolar square waves switching at 10 or 20 Hz was used. AC operation eliminates charge injection in the dielectric layers under very high electric fields, a problem observed after continuous DC actuation. Crucially, AC actuation thus allows the electrostatic force to be turned off as soon as the voltage is reduced, even after hours of continuous operation. It comes at the cost of marginally higher power consumption (but still far less than 1 W).

Glove Assembly

The ES brakes was mounted on a glove covering the index finger and the thumb via velcro fabric hook and loop fasteners, 3D printed guides (6 mm high and 14 mm wide) and 3D printed wrist and fingertip anchors (4.5 mm high and 16 mm wide), see FIG. 4. Assembly is straightforward and can account for variations of hand size, geometry (static) and flexibility (dynamic) across users.

Integration into VR

Tracking and Haptic Device Control

Creating a convincing method of grasping objects in VR requires precise tracking of the fingers in order to determine when contact has been made. For tracking, an Opti-Track tracking system was used with 10 Prime 13 W cameras running at 240 Hz and custom designed rigid-bodies that screw into the tips of the fingers. The centroids of the rigid-bodies are calibrated to sit in the center of the finger such that finger collisions in real life match finger collisions in VR. The mean tracking error after calibration of the whole system was <1 mm. An Oculus CV1 headset is used to display the virtual scene. The coordinate systems are aligned via a calibration procedure built into the Motive:Tracker software.

Unity software was used for rendering the VR scenes. The rigid-bodies, indicating the position of the fingers, are displayed as small spheres. Each haptic controller (index, thumb, piezo) has a separate physical connection (USB) and are controlled individually over different serial ports.

Grasping Method and Force Rendering

A custom grasping algorithm was implemented, using a kinematic approach. A grasp begins when the position of each finger (index, thumb) are within 5 mm of a virtual object and the object to be grasped is between the fingers. Once the object is grasped, the resulting ray between the two fingers is used to kinematically rotate and re-position the object in real time, and to calculate the amount of object penetration for analysis. The grasp ends when the ray between the fingers exceeds its original starting (euclidean) distance. This approach ensures a steady and natural feeling grasp and supports more types of grasps than off-the-shelf solutions such as the Leap Motion Interaction Engine.

As soon as a grasp begins, the electrostatic brake is engaged on both fingers by setting the HVS to output 1000V at 20 Hz, and stays activated until the end of the grasp, when it is set back to 0V. It is important not to simply cut the voltage instantly as some residual charge may remain on the 2 strips. By switching down the voltage instead, the charge is cleared faster, and fingers can retract without resistance.

The present description is neither intended nor should it be construed as being representative of the full extent and scope of the present invention. The present invention is set forth in various levels of detail herein as well as in the attached drawings and in the detailed description of the invention and no limitation as to the scope of the present invention is intended by either the inclusion or non-inclusion of elements, components, etc. in the description.

Exemplary embodiments have been described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined not solely by the claims. The features illustrated or described in connection with one exemplary embodiment may be combined with the features of other embodiments. Such modifications and variations are intended to be included within the scope of the present invention. A number of problems with conventional methods and systems are noted herein and the methods and systems disclosed herein may address one or more of these problems. By describing these problems, no admission as to their knowledge in the art is intended. A person having ordinary skill in the art will appreciate that, although certain methods and systems are described herein, the scope of the present invention is not so limited. Moreover, while this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A haptic device including an electrostatic brake configured to be attached to a body of a user, and configured to provide for a sliding friction to impede a movement of a joint of the body, the electrostatic brake comprising:
a first electrode including a conductive and flexible film, a first surface of the first electrode coated with dielectric material to cover the conductive film;
a first frame affixed to an end of the first electrode;
a second electrode including a conductive and flexible film, a second surface of the second electrode aligned parallel to the first surface of the first electrode such that the first and the second electrodes partially overlap;
a second frame affixed to an end of the second electrode;
a guiding structure for coupling the first and second electrodes to permit a linear movement relative to each other while keeping a partial overlap of the first and second surfaces of the first and second electrodes, respectively; and
a power source for applying a voltage between the first electrode and the second electrode to provide an electrostatic charge to cause an attractive force between the first and second electrodes and reversibly increase the sliding friction between the first and the second electrodes, wherein
the first and second electrodes are reversibly and elastically bendable to allow to bend with the movement of the joint.

2. The haptic device of claim 1, wherein none of the first frame, second frame, and the guiding structure are not interconnected with spring or tensioning elements.

3. The haptic device of claim 1, wherein the first and second frames include an attachment device for connecting the electrostatic brake to a body part of the user.

4. The haptic device of claim 1, wherein the overlap between the first and second surfaces of the first and the second electrodes, respectively, is between 10% and 100%.

5. The haptic device of claim 1, wherein the voltage applied by the power source is between 20 Volts and 5000 Volts.

6. The haptic device of claim 1, wherein the dielectric material has a thickness comprised between 0.5 µm and 50 µm.

7. The haptic device of claim 1, further comprising a glove for carrying the electrostatic brake.

8. A wearable device for virtual or augmented reality applications, including an electrostatic brake configured to be mounted on a body of a user, the electrostatic brake being according to claim 1.

9. A method for providing a kinaesthetic haptic feedback on a body of a user, the method comprising the steps of:
placing a haptic device as defined in claim 1 onto the body of the user such that the electrostatic brake is configured to hamper a movement of a body part; and
actuating the electrostatic brake.

10. The method of claim 9, wherein the body part is a finger or a hand.

11. A method for providing assisted grasping to a user, the method comprising the steps of:
placing a haptic device as defined in claim 1 onto a finger and/or a hand the user;
actuating the electrostatic brake to block a movement of the finger and/or the hand of the user to a certain position.

12. The haptic device of claim 1, wherein the guiding structure includes a plurality of guides arranged at different locations along a direction of longitudinal relative displacement of the first and second electrodes, each guide having a cavity, the cavity arranged to accommodate and hold together the first and second electrodes.

13. The haptic device of claim 1, wherein the first electrode including the conductive and flexible film and the dielectric material and the second electrode are formed as a longitudinal strips that is configured to be flexible, stretchable, and conformable to the movement of the joint.

14. A system for providing a kinaesthetic haptic feedback on the body of a user in a virtual or augmented reality application, the system comprising:
a haptic device including an electrostatic brake configured to be attached to a body of a user, and configured to provide for a sliding friction to impede a movement of a joint of the body, the electrostatic brake including,
a first electrode including a conductive and flexible film, a surface of the first electrode coated with dielectric material to cover the conductive film,
a first frame affixed to an end of the first electrode,
a second electrode including a conductive and flexible film, a surface of the second electrode aligned parallel to the surface of the first electrode such that the first and the second electrodes partially overlap,
a second frame affixed to an end of the second electrode, and
a guiding structure for coupling the first and second electrodes to permit a linear movement relative to each other while keeping a partial overlap of the surfaces of the first and second electrodes, respectively,
wherein the first and second electrodes are reversibly and elastically bendable to allow to bend with the movement of the joint;
a power source for applying a voltage between the first electrode and the second electrode to provide an electrostatic charge to cause an attractive force between the first and second electrodes and reversibly increase the sliding friction between the first and the second electrodes; and
a sensor including at least one of a position sensor, a force sensor, and a touch sensor.

15. The system of claim 14, further comprising a display device for displaying a virtual scene or object to the user.

16. The system of claim 14, wherein the guiding structure includes a plurality of guides arranged at different locations along a direction of longitudinal relative displacement of the first and second electrodes, each guide having a cavity, the cavity arranged to accommodate and hold together the first and second electrodes.

17. The system of claim 14, wherein the the first electrode including the conductive and flexible film and the dielectric material and the second electrode are formed as a longitudinal strips that is configured to be flexible, stretchable, and conformable to the movement of the joint.

* * * * *